United States Patent [19]
McMahon

[11] Patent Number: 5,782,804
[45] Date of Patent: Jul. 21, 1998

[54] NEEDLE RETRACTION MECHANISMS

[75] Inventor: Keith Herd Younie McMahon, Fife, United Kingdom

[73] Assignee: NMT Group PLC, Bellshill, United Kingdom

[21] Appl. No.: 776,422
[22] PCT Filed: Aug. 10, 1995
[86] PCT No.: PCT/GB95/01894
§ 371 Date: Jan. 29, 1997
§ 102(e) Date: Jan. 29, 1997
[87] PCT Pub. No.: WO96/05879
PCT Pub. Date: Feb. 29, 1996

[30] Foreign Application Priority Data

Aug. 18, 1994 [GB] United Kingdom ............... 9416710
May 5, 1995 [GB] United Kingdom ............... 9509224

[51] Int. Cl.$^6$ .................................................. A61M 5/00
[52] U.S. Cl. .......................... 604/110; 604/195; 604/243; 128/919
[58] Field of Search ........................... 604/110, 195, 604/187, 181, 192, 198, 218, 191, 194, 227, 239–243; 128/919, 917

[56] References Cited

U.S. PATENT DOCUMENTS

| | | | |
|---|---|---|---|
| 4,650,468 | 3/1987 | Jennings, Jr. | 604/110 |
| 4,695,274 | 9/1987 | Fox | 604/198 |
| 4,767,413 | 8/1988 | Haber et al. | 604/198 |
| 4,790,822 | 12/1988 | Haining | 604/110 |
| 4,804,370 | 2/1989 | Haber et al. | 604/195 |
| 4,813,936 | 3/1989 | Schroeder | 604/195 |
| 4,826,484 | 5/1989 | Haber et al. | 604/110 |
| 4,826,489 | 5/1989 | Haber et al. | 604/195 |
| 4,861,338 | 8/1989 | Mathiesen et al. | 604/110 |
| 4,904,242 | 2/1990 | Kulli | 604/110 |
| 4,908,022 | 3/1990 | Haber | 604/195 |
| 5,019,044 | 5/1991 | Tsao | 604/195 |
| 5,084,018 | 1/1992 | Tsao | 604/195 |
| 5,114,404 | 5/1992 | Paxton et al. | 604/110 |
| 5,180,369 | 1/1993 | Dysarz | 604/195 |
| 5,180,370 | 1/1993 | Gillespie | 604/195 |
| 5,188,599 | 2/1993 | Botich et al. | 604/198 |
| 5,201,710 | 4/1993 | Caselli | 604/195 |
| 5,211,629 | 5/1993 | Pressly et al. | 604/110 |
| 5,242,402 | 9/1993 | Chen | 604/110 |
| 5,385,551 | 1/1995 | Shaw | 604/110 |
| 5,407,436 | 4/1995 | Toft et al. | 604/195 |

*Primary Examiner*—Ronald Stright, Jr.
*Attorney, Agent, or Firm*—James E. Bradley

[57] ABSTRACT

A fluid handling device has a needle retraction assembly which brings about the retraction of a hollow needle after use. A hollow body portion is provided at one end, with an end wall having a mounting portion including a needle passage. A hollow needle having a leading end portion is movable between a first position in which the leading end portion of the needle protrudes from a front end portion of said mounting portion and a second position in which the needle is withdrawn within the hollow body portion. A spring acts to bias the needle into the second, withdrawn position. The needle is provided with a portion of enlarged diameter at a location spaced from the leading end portion. A retainer maintains the needle in its first position until use is completed. The retainer includes an O-ring positioned in a circumferential groove in the portion of enlarged diameter. The O-ring abuts the end of a sleeve slidable within the mounting portion and which can be forced forwardly to dislodge the O-ring so as to permit the needle to move from its first position into its second position under the influence of the spring.

12 Claims, 5 Drawing Sheets

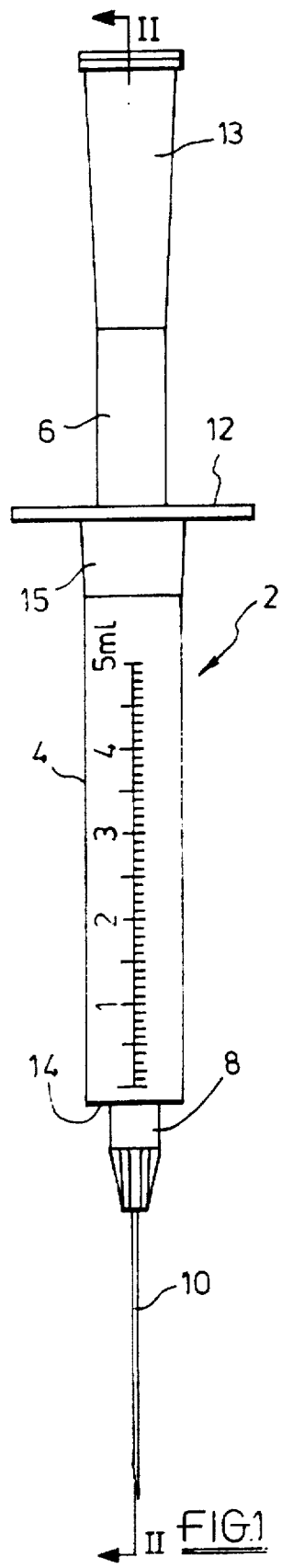
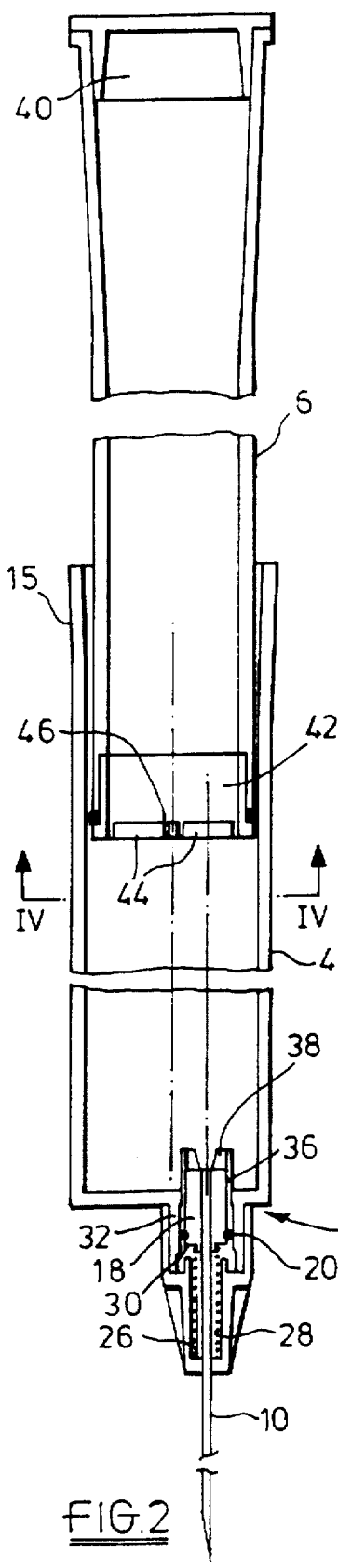
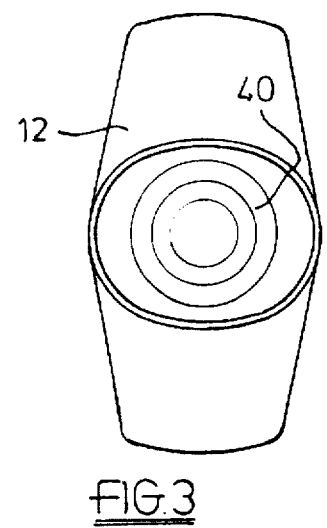
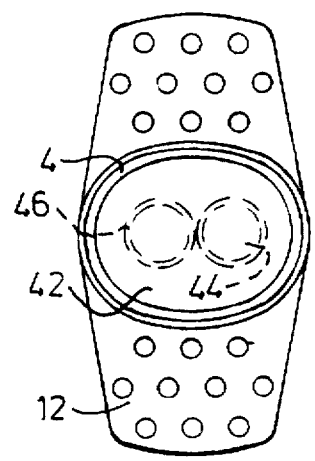
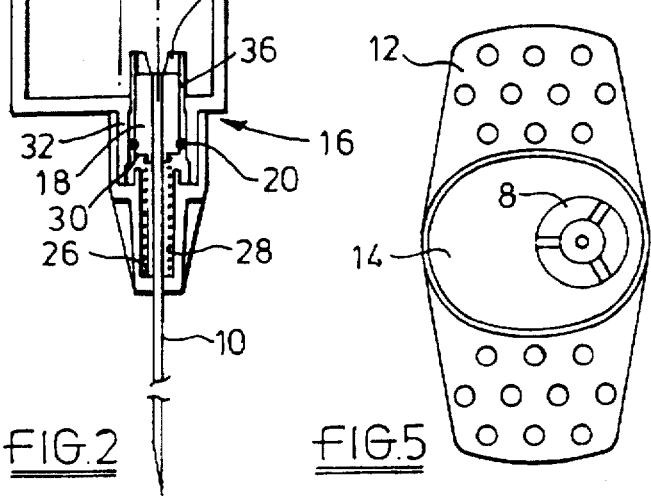

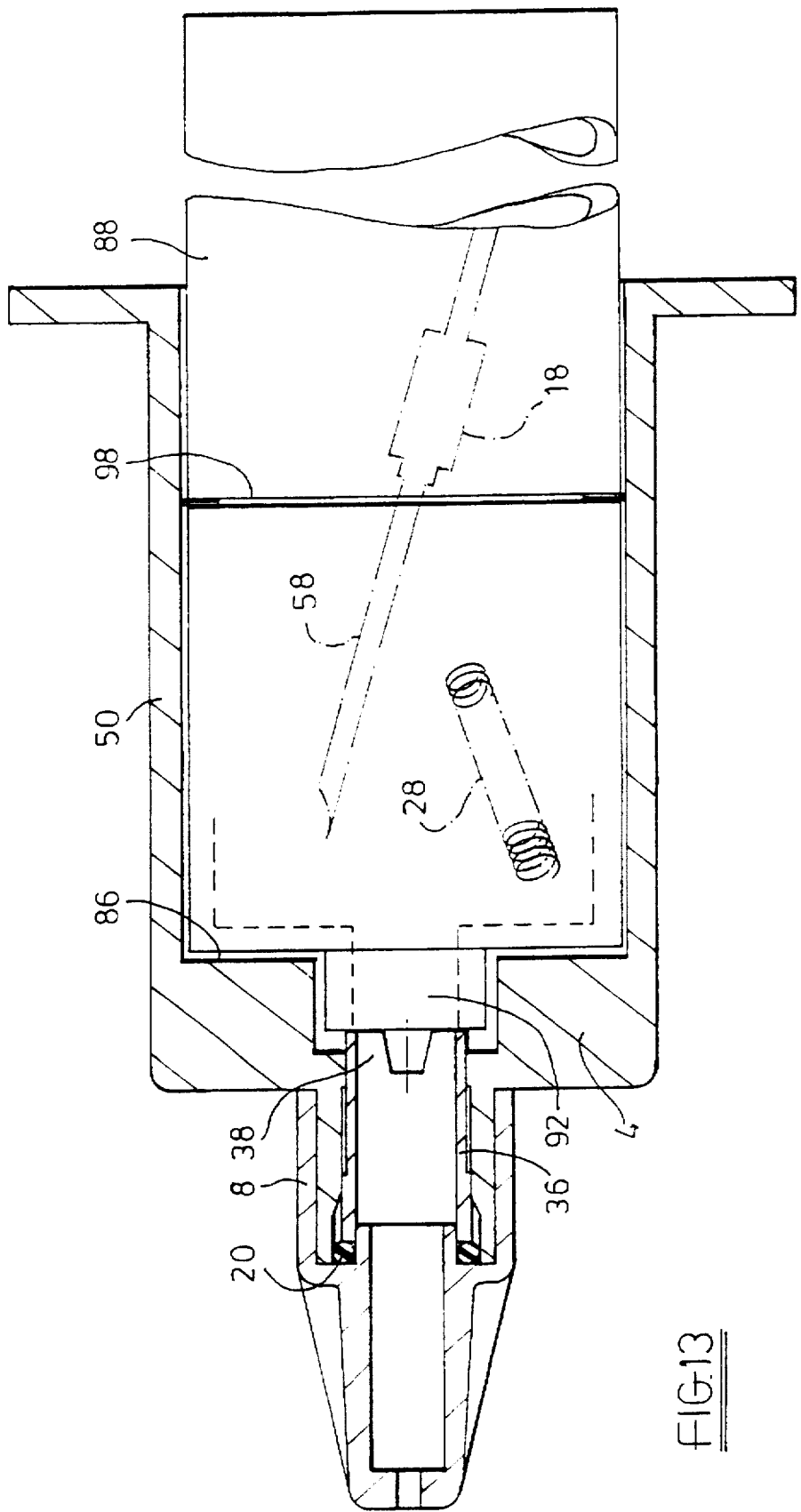

NEEDLE RETRACTION MECHANISMS

BACKGROUND OF THE INVENTION

1. Field of Invention

The invention is concerned with improvements in or relating to retraction mechanisms for use in fluid handling devices, said mechanisms being arranged to bring about the retraction of a hollow needle into a housing after use. Such devices are used in many facets of the medical field, for the administration of drugs or a drip feed into a blood vessel, or for drawing off liquid samples, for example, blood from patients.

2. Description of the Related Art

It will be understood that there is a wide range of fluid handling devices incorporating needles in use in the field of medicine for the administration of drugs and the like for blood sampling, including use in procuring more than one sample from a patient over a period of time.

It is important that the needles of such devices, which are frequently intended for disposal after a single use, are rendered inoperative to prevent accidental injury or re-use with the substantial risk of cross-contamination.

Syringes provided with guards of one kind or another which are automatically deployed to shield the needle after use are known, as are syringes where the needle is automatically retracted after use into the body of the device.

The invention provides a fluid handling device having a needle retraction assembly adapted to bring about the retraction of a hollow needle after use comprising a hollow body portion provided at one end thereof with an end wall having a mounting portion including a needle passage, and a hollow needle having a mounting means and adapted to be movable between a first position in which a leading end portion of the needle protrudes from a front end portion of said mounting portion and a second position in which the needle is withdrawn within the hollow body portion, said mounting means including resilient means that act to bias the needle into the second, withdrawn, position, said needle being provided with an enlarged portion at a location spaced from the leading end portion thereof, there being provided retaining means to maintain the needle in its first position until use is completed, said retaining means comprising in combination an O-ring positioned in a circumferential groove in said enlarged portion and abutting the end of a sleeve which can be forced forwardly to dislodge the O-ring so as to permit the needle to move from its first position into its second position under the influence of said resilient means.

The sleeve may be restrained from rearward movement when the needle is in its first position by a shoulder which abuts a flange at the forward end of the body portion.

The resilient means may be a compression spring located between a forward reaction surface provided by the mounting portion and a rearward reaction surface provided by the forward end of the enlarged portion.

When the needle is in its first position the O-ring may be compressed between the enlarged portion and the mounting portion, which provides a relieved part at its forward end to receive the O-ring when it is dislodged.

The fluid handling device may be a syringe, there being a piston which may be depressed to travel through the body portion to discharge liquid therefrom through the needle, the piston being in the form of a tube having closed ends, the forward of which is provided with a closure member which is separable from the end by engagement with the sleeve as the piston is fully depressed to provide an aperture in the end through which the needle may pass to enter the interior of the piston as it assumes its second position.

The mounting portion may be off-centre and towards a peripheral edge of the body portion.

The cross-sections of the body portion and piston may be such as to prohibit incorrect assembly having regard to the position of the closure member.

The cross-sections of the body portion and piston may be such that whilst permitting assembly in more than one rotational position relative to one another, proper operation is assured, there being more than one closure member in the end of the piston.

The body portion and piston may be of elliptical section, there being two spaced closure members in the end of the piston.

The hollow body portion may not be intended to receive a piston, and a piston-like tool may be inserted into the body portion to cause retraction of the needle into the tool when desired.

The sleeve may be located in a recess accessible by a portion of reduced size on the forward end of the tool adapted to enter the recess to engage with the sleeve. This prevents premature retraction of the needle.

BRIEF DESCRIPTION OF THE DRAWINGS

FIG. 1 is a side view of a syringe according to the invention, in an unused condition;

FIG. 2 is a longitudinal section of the syringe taken on line II—II of FIG. 1 and to an enlarged scale;

FIG. 3 is an end view of the syringe;

FIG. 4 is a section on lines IV—IV of FIG. 2;

FIG. 5 is an opposite end view, being a needle end view;

FIG. 13 is a view of the device with the needle thereof in a retracted condition.

DESCRIPTION OF THE PREFERRED EMBODIMENT

Figure 6:
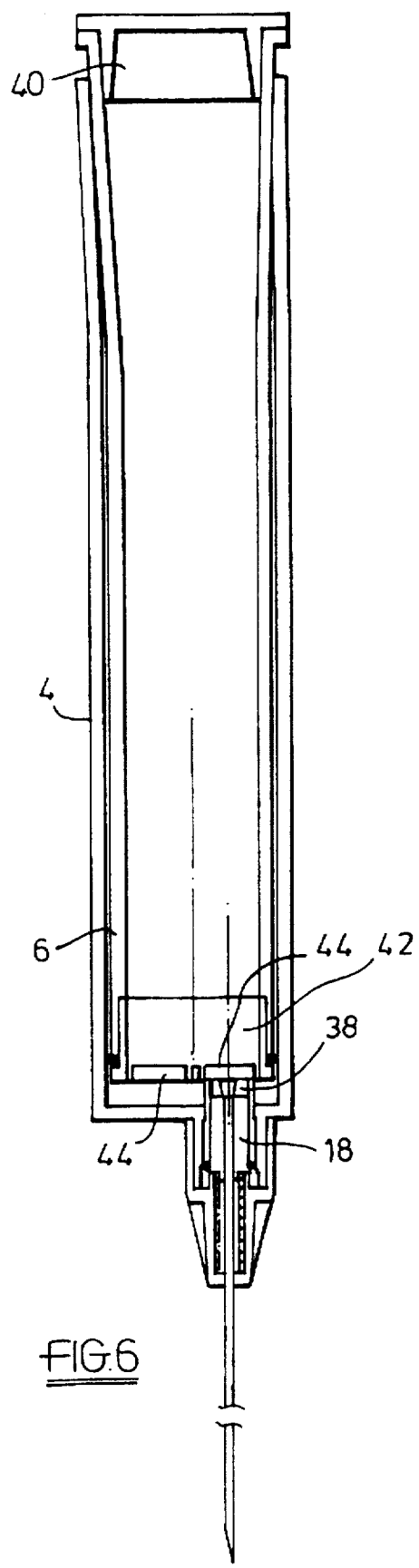
FIG. 6 is a sectional view similar to FIG. 1 illustrating an intermediate stage in the depression of a plunger of the syringe.
Figure 7:
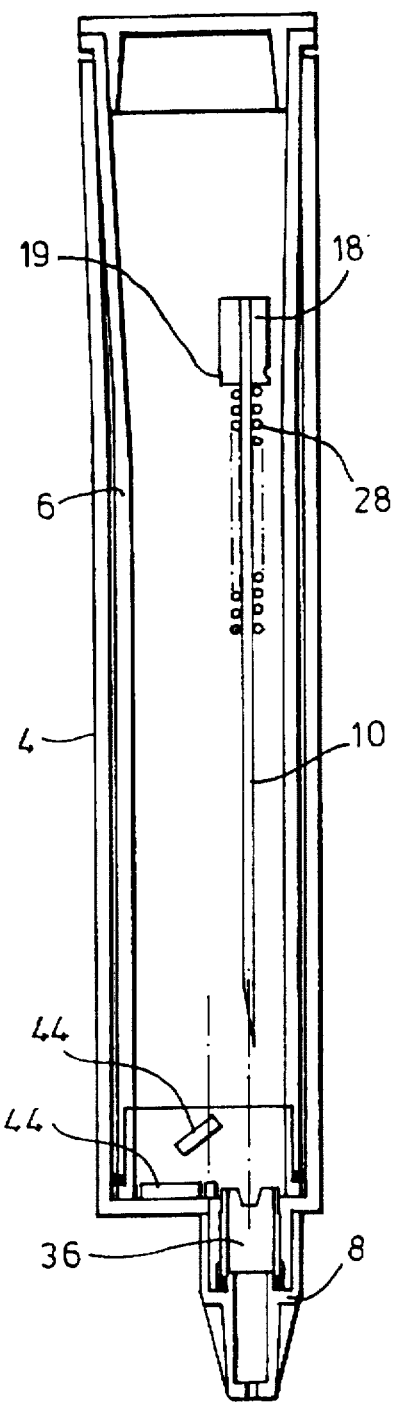
FIG. 7 is a similar view illustrating the completion of the depression step.

A disposable syringe 2 is shown in FIG. 1 comprising a hollow body portion 4, from the rear of which (upper end as viewed in FIG. 1) protrudes a piston 6. At the lower end of the body portion 4 is provided a mounting portion 8 for a needle 10, having a through passage at the inner end of which is an upstanding annular wall 9.

The hollow body portion 4, which is non-opaque, is graduated in millilitres for convenience and is provided with finger-engaging flanges 12 in the conventional manner. The body portion 4 has a slightly outwardly flared end portion 15. The mounting portion 8 is secured to an end wall 14 of the body portion 4 in an off-centre position at 16 (see FIG. 2) to facilitate use of the syringe in enabling the needle 10 to penetrate tissue or a blood vessel at as shallow an angle as desired.

The inner end of the needle 10 connects with a collar 18 having an annular groove 19 in which is received an O-ring 20. Groove 19 provides a shoulder against which the O-ring 20 abuts. The collar 18 is bonded to the needle so as to be integral therewith.

As best seen from FIGS. 3 to 5 the body portion 4 and piston 6 are of elliptical section which avoids any tendency for unwanted relative rotation of the parts.

The mounting portion 8 provides a passageway for the needle 10 and provides a first reaction surface 26 for a compression spring 28 surrounding the needle. A second reaction surface 30 is provided on a forward end of the collar 18. When assembled the spring 28 is in an almost fully compressed condition between the surfaces 26 and 30 and is maintained in that condition by engagement of the O-ring 20, which is compressed between an annular wall portion 32 of the mounting part 8 and its groove 19, with an end surface 34 of a sleeve 36 surrounding the collar 18 and comprising at its rearward end an extension 38, formed by lugs, which project into the hollow body portion 4 in the pre-use condition shown in FIGS. 2 and 8.

Figure 8:
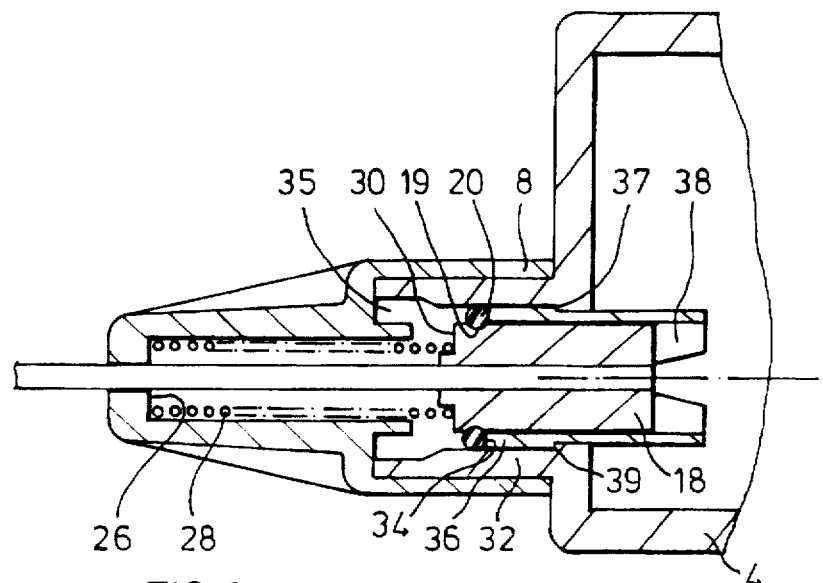
FIGS. 8, 9 and 10 are fragmentary views to an enlarged scale of portions of FIGS. 2, 6 and 7 respectively.

As may be seen in FIG. 8, an annular space 35 is provided to the forward side of O-ring 20.

The sleeve 36 has a shoulder 37 which engages an annular flange 39 at the forward end of the body 4 to prevent rearward movement of the sleeve 36 from its initial position shown in FIGS. 2 and 8.

The piston 6 is hollow having its rear end closed by means of a cap 40. It will be noticed that the diameter of the piston is greatest at the rear end of the piston at 13, that is, adjacent the end cap 40 and tapers inwardly towards the body portion.

The other end of the piston is arranged to receive a closure member 42 which engages firmly in the piston to form an end wall having two areas 44 defined by lines of weakness 46 so as to be readily removed on contact with the sleeve extension lugs 38 in a manner to be explained below. The provision of two such areas 44 obviates the need to check the position of the off-set needle 10 during assembly.

In operation, the syringe is conveniently charged with liquid in a normal manner, to achieve its ready-for-use condition in which the piston 6 is received within the body portion 4 by a short distance as shown in FIG. 2. The closure member 42 of the piston thus also acts as a seal for the liquid contents of the body portion.

Figure 9:
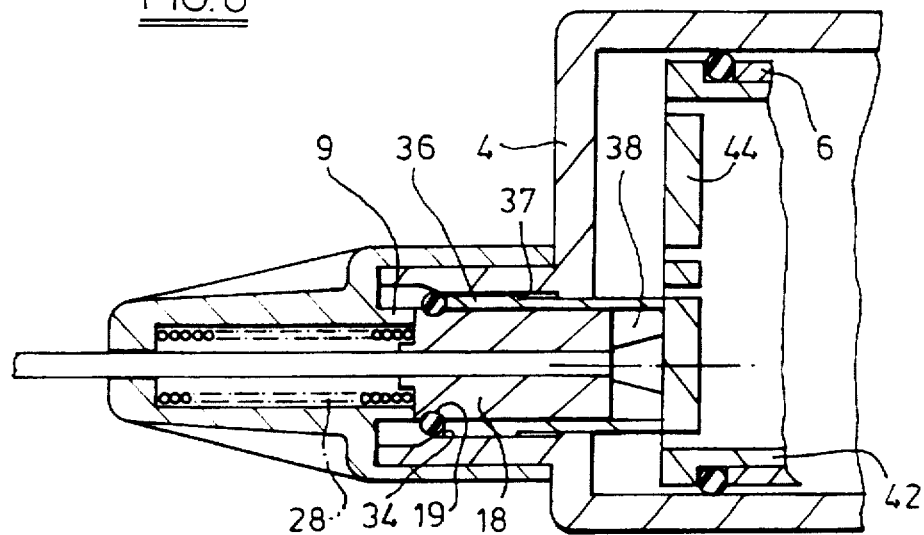
Figure 10:
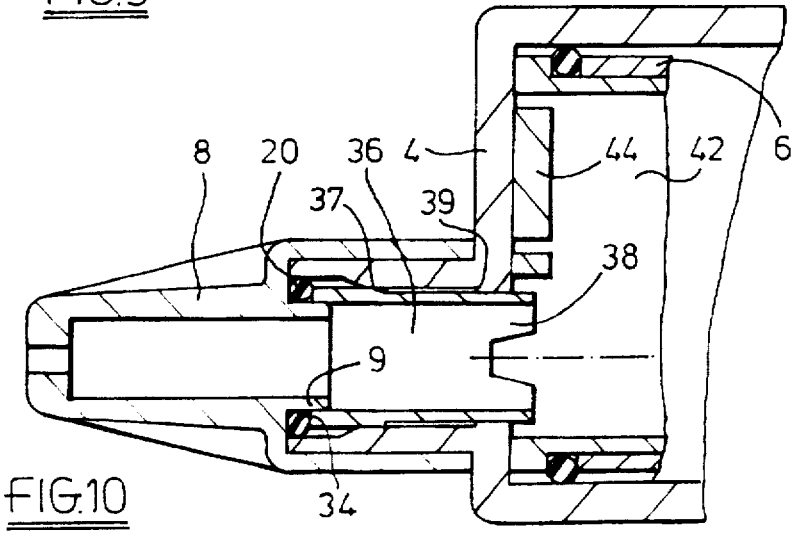

On actuation of the piston 6 so as to move forwardly (or downwardly as viewed in the FIG. 1), the advance of the end wall of the member 42 expels the liquid through the needle 10. FIG. 9 shows the position of the parts immediately before the expulsion of the liquid is completed. It will be observed that the end wall of the member 42 has contacted the lugs 38 of the sleeve member 36 and has forced the member 36 forwardly as shown in FIGS. 9. However, liquid may still pass from the body portion 4 to the needle 10 due to the spaces between the lugs 38 of the sleeve 36. In FIG. 10, the movement of the sleeve member 36, because of its contact with the O-ring 20 that is received in the groove 19, has caused the collar 18 also to move forwardly, further compressing the spring 28 to a fully compressed state. In addition, this movement causes the O-ring 20 to be released from entrapment in the groove 19 by the annular portion 32 and to be dislodged from the shoulder to enter the annular space 35, where it is received over the wall 9 of the mounting portion 8. Thus the restraint acting upon the needle end portion 18 is removed. The fully compressed spring 28 is now no longer constrained and extends rapidly, propelling the needle end portion 18 and therefore also the needle itself rearwardly. The sleeve member 36 and its lugs 38 are together of such a length as still to project into the hollow interior of the body portion 4. The lugs therefore provide a pressure area against the area 44 so as to shear the line of weakness 46. The needle 10 is thus free to pass through the sleeve member 36 into the hollow interior of the piston 6, so that the needle is withdrawn from access by potential re-users of the syringe. It will be understood that the piston 6 cannot in practice readily be withdrawn from the body portion 4 to facilitate access to the needle, since the annular portion 13 of the piston 6 is firmly wedged into the flared end portion 15 of the body portion 4 and thus resists removal.

The syringe may therefore now be disposed of without risk to persons subsequently handling the needle.

Figure 11:
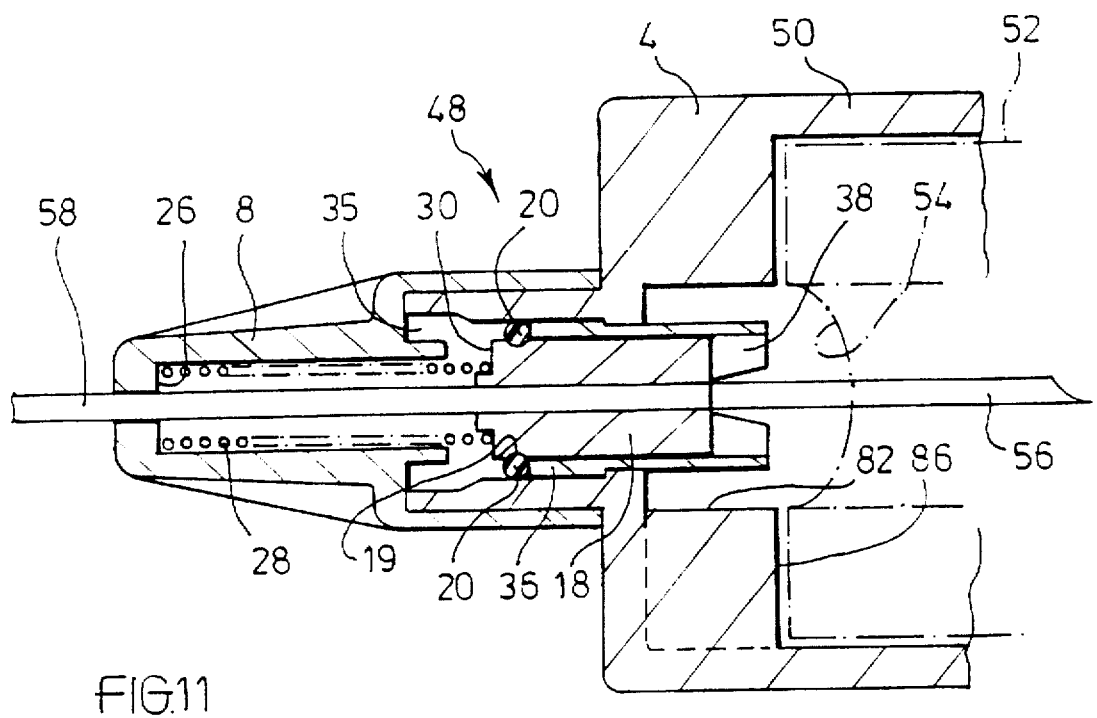
FIG. 11 is a fragmentary longitudinal sectional view of a fluid handling device for taking blood samples.

FIG. 11 shows a fragmentary view of a needle retraction mechanism indicated at 48, for use in a device for taking repeated blood samples. The device comprises an open-ended housing 50 into which is inserted an evacuated tube 52 of the kind sold under the Registered Trade Mark "Vacutainer", having a diaphragm 54 which is pierced by a rear end portion 56 of a double-ended hollow needle 58 so that the sample may be drawn into the tube 52. Conveniently, the needle 58 may remain in place during the period of time in which it may be necessary to take a series of samples, but when the series is completed, the needle must be removed and the risks associated with used needles then arise.

Figure 12:
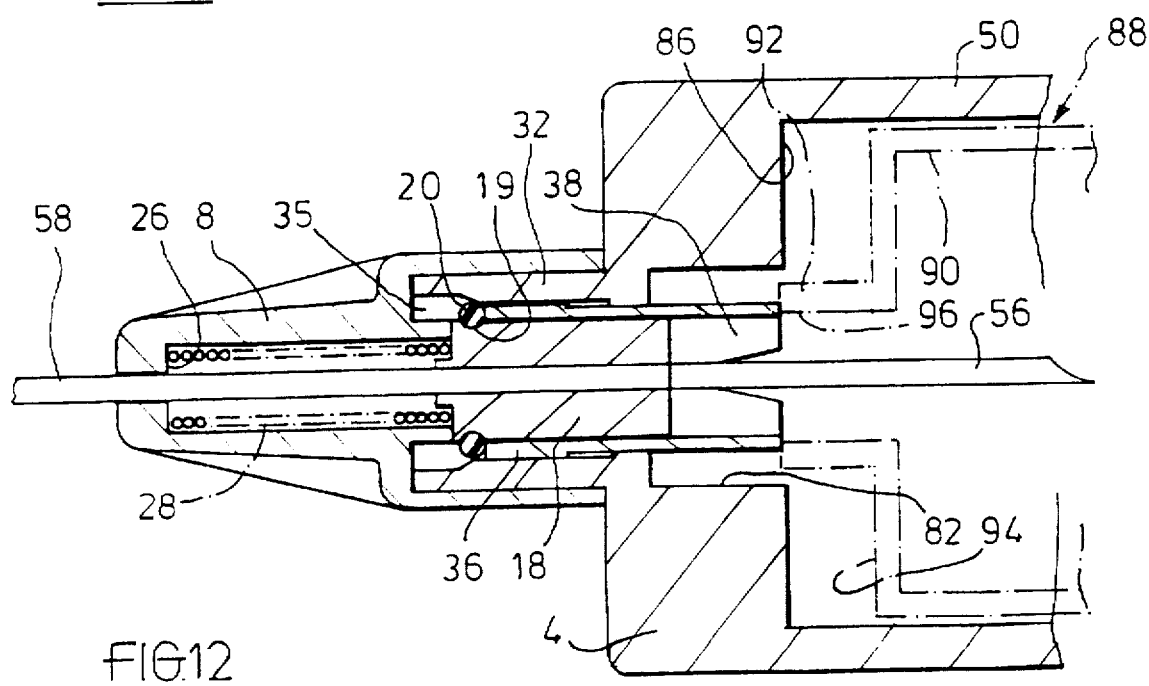
FIG. 12 is a similar view with a needle retraction tool inserted therein.

The needle retraction mechanism of the device of FIGS. 11 to 13 is similar in many respects to that shown in the syringe of FIGS. 1 to 10, like parts being indicated by like reference numerals.

The needle 58 which as mentioned above is double-ended and passes through the collar 18.

A recessed portion 82 is formed in the forward wall of the housing 50 which has a surface 86 against which the evacuated tube 52 abuts in normal use. Thus in normal use, it will be observed, no contact is made by the tube 52 with the lugs 38.

FIG. 12 illustrates the means by which the needle 58 may be retracted out of an operative condition and into a position which it cannot be used again nor can it injure anyone handling it.

Thus when the final sample has been taken and the needle of the device needs to be removed from the patient's arm, a tool 88 is inserted into the housing 50 as shown in FIG. 12. The tool 88 comprises plunger-like hollow body portion 90 and an annular projection or neck 92 that is surrounded by a shoulder surface 94. The neck 92 has a circular opening 96. As the tool 88 is inserted into the housing 50, the needle end portion 56 enters the opening 96 in the neck 92 and the neck itself enters the recess 82 in the housing 50. The leading edge surface of the neck 92 contacts the lugs 38 and continued pressure applied to move the tool forwardly as shown in FIG. 12 causes the sleeve member 36 to move forwardly to dislodge the O-ring 20 to release the needle 58 for discharge into the body of the tool 88. A snap-on ring clip 98 around the tool 88 ensures that the tool is not accidentally removed from the housing 50 before safe disposal.

Various modifications may be made within the scope of the invention as defined by the following claims.

I claim:

1. A fluid handling device having a needle retraction assembly adapted to bring about the retraction of a hollow needle after use, said fluid handling device comprising:

a hollow body portion provided at one end thereof with an end wall having a hollow mounting portion, said mounting portion comprising an annular wall extending distally from said end wall, said mounting portion further including a distal wall having a needle passage therethrough;

a hollow needle having a tissue penetrating end portion and being adapted to be movable between a first position in which the tissue penetrating end portion of the needle protrudes from said needle passage of said hollow mounting portion and a second position in which the needle is withdrawn completely within the hollow body portion, said needle being provided with a collar portion of enlarged diameter at a location spaced from the tissue penetrating end portion thereof, and being located within said hollow mounting portion;

an O-ring positioned against a circumferential shoulder on said collar portion of enlarged diameter and said annular wall of said mounting portion for providing a fluid seal therebetween as well as for retaining the needle in its first position until use is completed;

a spring located between said distal wall of said mounting portion and a distal end of said collar portion of enlarged diameter, said spring for biasing said needle into the second position within said hollow body portion; and a sleeve located around said collar portion of enlarged diameter and within the hollow mounting portion of said hollow body portion, said sleeve having a distal end in contact with said O-ring, said sleeve being slidable within the mounting portion and which can be forced forwardly to dislodge the O-ring from said shoulder so as to permit the needle to move automatically from its first position into its second position under the influence of said spring.

2. The fluid handling device according to claim 1, wherein said device is a syringe, said syringe having a hollow piston within said body portion which may be depressed to travel through said body portion to discharge liquid therefrom through the needle, the piston being in the form of a tube having closed ends, the forward of which is provided with a closure member which is separable from the end by engagement with said sleeve as the piston is fully depressed to provide an aperture in the forward end through which the needle may pass to enter the interior of the piston as it assumes its second position.

3. The fluid handling device according to claim 2 wherein the mounting portion is off-center and towards a peripheral edge of the body portion.

4. The fluid handling device according to claim 3, wherein the cross-sections of the body portion and piston are such as to prohibit assembly with the closure member offset from the needle.

5. The fluid handling device according to claim 1 wherein a hollow tool may be insertable into the body portion to slide the sleeve forwardly to cause dislodge said O-ring to retraction of the needle into the tool when desired.

6. The fluid handling device according to claim 5 wherein a proximal end of said sleeve is located in a recess within said end wall of said hollow body accessible by a portion of reduced size on the forward end of the tool said proximal end of said sleeve adapted to enter said recess to engage with said sleeve.

7. The fluid handling device according to claim 1, wherein said mounting portion has an area of enlarged internal diameter at its forward end to receive the O-ring when it is dislodged.

8. A fluid handling device having a needle retraction assembly adapted to bring about the retraction of a hollow needle after use, said fluid handling device comprising:

a hollow body portion provided at one end thereof with an end wall having a hollow mounting portion, said mounting portion comprising an annular wall extending distally from said end wall, said mounting portion further including a distal wall having a needle passage therethrough;

a hollow needle having a tissue penetrating end portion and being adapted to be movable between a first position in which the tissue penetrating end portion of the needle protrudes from said needle passage of said hollow mounting portion and a second position in which the needle is withdrawn completely within the hollow body portion, said needle being provided with a collar portion of enlarged diameter at a location spaced from the tissue penetrating end portion thereof, and being located within said hollow mounting portion;

an O-ring positioned against a circumferential shoulder on said collar portion of enlarged diameter and said annular wall of said mounting portion for providing a fluid seal therebetween as well as for retaining the needle in its first position until use is completed;

a spring located between said distal wall of said mounting portion and a distal end of said collar portion of enlarged diameter, said spring for biasing said needle into the second position within said hollow body portion; and a sleeve located around said collar portion of enlarged diameter and within the hollow mounting portion of said hollow body portion, said sleeve having a distal end in contact with said O-ring, said sleeve being slidable within the mounting portion and which can be forced forwardly to dislodge the O-ring from said shoulder so as to permit the needle to move automatically from its first position into its second position under the influence of said spring, wherein said sleeve is restrained from rearward movement when the needle is in its first position by a shoulder on said sleeve which abuts a flange on said annular wall of said mounting portion.

9. The fluid handling device according to claim 8, wherein said device is a syringe, said syringe having a hollow piston within said body portion which may be depressed to travel through said body portion to discharge liquid therefrom through the needle, the piston being in the form of a tube having closed ends, the forward of which is provided with a closure member which is separable from the end by engagement with said sleeve as the piston is fully depressed to provide an aperture in the forward end through which the needle may pass to enter the interior of the piston as it assumes its second position.

10. A fluid handling device having a needle retraction assembly adapted to bring about the retraction of a hollow needle after use, said fluid handling device comprising:

a hollow body portion provided at one end thereof with an end wall having a hollow mounting portion, said mounting portion comprising an annular wall extending distally from said end wall, said mounting portion further including a distal wall having a needle passage therethrough;

a hollow needle having a tissue penetrating end portion and being adapted to be movable between a first position in which the tissue penetrating end portion of the needle protrudes from said needle passage of said hollow mounting portion and a second position in which the needle is withdrawn completely within the hollow body portion, said needle being provided with a collar portion of enlarged diameter at a location spaced from the tissue penetrating end portion thereof, and being located within said hollow mounting portion;

an O-ring positioned against a circumferential shoulder on said collar portion of enlarged diameter and said annular wall of said mounting portion for providing a fluid seal therebetween as well as for retaining the needle in its first position until use is completed;

a spring located between said distal wall of said mounting portion and a distal end of said collar portion of enlarged diameter, said spring for biasing said needle into the second position within said hollow body portion; and a sleeve located around said collar portion of enlarged diameter and within the hollow mounting portion of said hollow body portion, said sleeve having a distal end in contact with said O-ring, said sleeve being slidable within the mounting portion and which can be forced forwardly to dislodge the O-ring from said shoulder so as to permit the needle to move automatically from its first position into its second position under the influence of said spring, further comprising a hollow piston which may be depressed to travel through the body portion to discharge liquid therefrom through the needle, the piston being in the form of a tube having closed ends, the forward of which is provided with a closure member which is separable from the end by engagement with said sleeve as the piston is fully depressed to provide an aperture in the forward end through which the needle may pass to enter the interior of the piston as the needle assumes its second position.

wherein the mounting portion is off-center and towards a peripheral edge of the body portion, and wherein said piston comprises more than one closure member in the forward end thereof, said body portion and said piston having a cross-section permitting assembly in more than one rotational position relative to one another.

11. The syringe according to claim 10 wherein the body portion and piston are of elliptical cross section and wherein said more than one closure member comprises two spaced closure members in the end forward of the piston.

12. The fluid handling device according to claim 10, wherein said device is a syringe, said syringe having a hollow piston within said body portion which may be depressed to travel through said body portion to discharge liquid therefrom through the needle, the piston being in the form of a tube having closed ends, the forward of which is provided with a closure member which is separable from the end by engagement with said sleeve as the piston is fully depressed to provide an aperture in the forward end through which the needle may pass to enter the interior of the piston as it assumes its second position.

* * * * *

UNITED STATES PATENT AND TRADEMARK OFFICE
CERTIFICATE OF CORRECTION

PATENT NO. : 5,782,804
DATED : July 21, 1998
INVENTOR(S) : Keith Herd Younie McMahon It is certified that error appears in the above-identified patent and that said Letters Patent is hereby corrected as shown below:

Title page,
Under References Cited, add the following list of patents,

| | | | |
|---|---|---|---|
| -- 5,423,758 | 06/1995 | Shaw | 604/110 |
| 5,389,076 | 02/1995 | Shaw | 604/110 |
| 5,267,961 | 12/1993 | Shaw | 604/110 |
| 5,188,613 | 02/1993 | Shaw | 604/195 |
| 5,120,310 | 06/1992 | Shaw | 604/110 |
| 5,114,410 | 05/1992 | Caralt Batlle | 604/195 |
| 5,092,853 | 03/1992 | Couvertier, II | 604/195 |
| 5,064,419 | 11/1991 | Gaarde | 604/195 |
| 5,053,010 | 10/1991 | McGary et al. | 604/110 |
| 5,049,133 | 09/1991 | Villen Pascual | 604/110 |
| 5,000,738 | 03/1991 | LaVallo et al. | 604/110 |
| 5,000,736 | 03/1991 | Kaufhold, Jr. et al. | 604/110 |
| 4,994,034 | 02/1991 | Botich et al. | 604/110 |
| 4,978,343 | 12/1990 | Dysarz et al. | 604/195 |
| 4,973,316 | 11/1990 | Dysarz | 604/195 |
| 4,966,592 | 10/1990 | Burns et al. | 604/198 |
| 4,955,870 | 09/1990 | Ridderheim et al. | 604/195 |
| 4,950,241 | 08/1990 | Ranford | 604/110 |
| 4,946,446 | 08/1990 | Vadher | 604/198 |
| 4,927,414 | 05/1990 | Kulli | 604/110 |
| 4,921,486 | 05/1990 | DeChellis et al. | 604/110 |
| 4,908,022 | 03/1990 | Haber | 604/195 |
| 4,900,307 | 02/1990 | Kulli | 604/110 |
| 4,874,382 | 10/1989 | Lindemann et al. | 604/195 |
| 4,838,869 | 06/1989 | Allard | 604/195 |
| 4,838,863 | 06/1989 | Allard et al. | 604/110 |
| 4,826,489 | 05/1989 | Haber et al. | 604/195 |

UNITED STATES PATENT AND TRADEMARK OFFICE
CERTIFICATE OF CORRECTION

PATENT NO. : 5,782,804  
DATED : July 21, 1998  
INVENTOR(S) : Keith Herd Younie McMahon Page 2 of 2

It is certified that error appears in the above-identified patent and that said Letters Patent is hereby corrected as shown below:

| | | | |
|---|---|---|---|
| 0210160 | 01/1987 | EP | A61M 5/18 |
| 0438368AI | 07/1991 | EP | A61M 5/32 |
| 0413414AI | 02/1991 | EP | A61M 5/50 |
| 0609167AI | 08/1994 | EP | A61M 5/32 |
| WO89/00435 | 01/1989 | PCT | A61M 5/28 |
| WO94/04207 | 03/1994 | PCT | A61M 5/24 |
| 2242631 | 11/1989 | GB | A61M 5/32 |
| 225161 | | JP | |
| 152558 | 04/1979 | JP | A61M |
| 154735 | 06/1979 | JP | A61M -- |

Signed and Sealed this

Sixteenth Day of April, 2002

Attest:

Attesting Officer

JAMES E. ROGAN  
*Director of the United States Patent and Trademark Office*